United States Patent [19]
Chow

[11] Patent Number: 5,448,160
[45] Date of Patent: Sep. 5, 1995

[54] PARTICLE SIZE PROBE FOR SILVER HALIDE EMULSION

[75] Inventor: Lu Chow, Fairport, N.Y.

[73] Assignee: Eastman Kodak Company, Rochester, N.Y.

[21] Appl. No.: 182,529

[22] Filed: Jan. 14, 1994

Related U.S. Application Data

[63] Continuation of Ser. No. 912,941, Jul. 13, 1992, abandoned.

[51] Int. Cl.$^6$ ............................................. G01N 27/00
[52] U.S. Cl. ................................. 324/71.1; 324/72; 430/30; 430/567; 430/569
[58] Field of Search .................... 324/71.1, 72, 72.5, 324/149; 430/30, 567, 569

[56] References Cited

U.S. PATENT DOCUMENTS

| | | | |
|---|---|---|---|
| 3,681,136 | 8/1972 | Leonard et al. | 427/126.1 |
| 3,882,385 | 5/1975 | Coulter et al. | 324/71.1 |
| 3,894,917 | 7/1975 | Riseman et al. | 204/1 T |
| 4,026,668 | 5/1977 | Culhane et al. | 422/110 |
| 4,172,777 | 10/1979 | Yamamoto et al. | 204/195 R |
| 4,198,160 | 4/1980 | Kachel et al. | 356/72 |
| 4,237,416 | 12/1980 | Zöld | 324/71.1 |
| 4,263,010 | 4/1981 | Randolph | 23/230 A |
| 4,437,970 | 3/1984 | Kitajima et al. | 204/412 |
| 4,585,733 | 4/1986 | Ezaki et al. | 430/569 |
| 4,746,093 | 5/1988 | Kitchin et al. | 430/567 X |
| 4,849,194 | 7/1989 | Krishnamurthy et al. | 423/328 |
| 4,883,579 | 11/1989 | Humphries et al. | 324/71.5 X |
| 4,895,705 | 1/1990 | Wrighton et al. | 422/68 |
| 4,945,036 | 7/1990 | Arai et al. | 430/567 |
| 4,966,670 | 10/1990 | Calzi | 204/406 |
| 5,035,991 | 7/1991 | Ichikawa et al. | 430/569 |
| 5,049,247 | 9/1991 | Nyberg et al. | 204/153.1 |
| 5,254,454 | 10/1993 | Mimiya et al. | 430/569 |
| 5,270,159 | 12/1993 | Ichikawa | 430/569 |
| 5,272,027 | 12/1993 | Dillenbeck et al. | 430/30 |

FOREIGN PATENT DOCUMENTS

| | | |
|---|---|---|
| 0188319 | 7/1986 | European Pat. Off. . |
| 58-034352 | 5/1983 | Japan . |
| 3197323 | 11/1991 | Japan . |

*Primary Examiner*—Kenneth A. Wieder
*Assistant Examiner*—Glenn W. Brown
*Attorney, Agent, or Firm*—Carl F. Ruoff

[57] ABSTRACT

The present invention concerns a method and apparatus for determining average particle size of silver halide grains in a solution or emulsion containing silver ions and excess halide ions. The potential of the silver ion in solution ($E_d$) is measured using a silver electrode and the potential of the silver ion in solution with infinitely large silver halide particles ($E_e$) is measured using a silver electrode coated with silver halide. The molecular volume (v) of the solute is calculated and the average particle size (d) is calculated from the following formula:

$$d = \frac{4 v s}{F(E_d - E_e)}$$

wherein F is the Faraday constant and (s) is the surface energy of the average particle size per unit area.

20 Claims, 3 Drawing Sheets

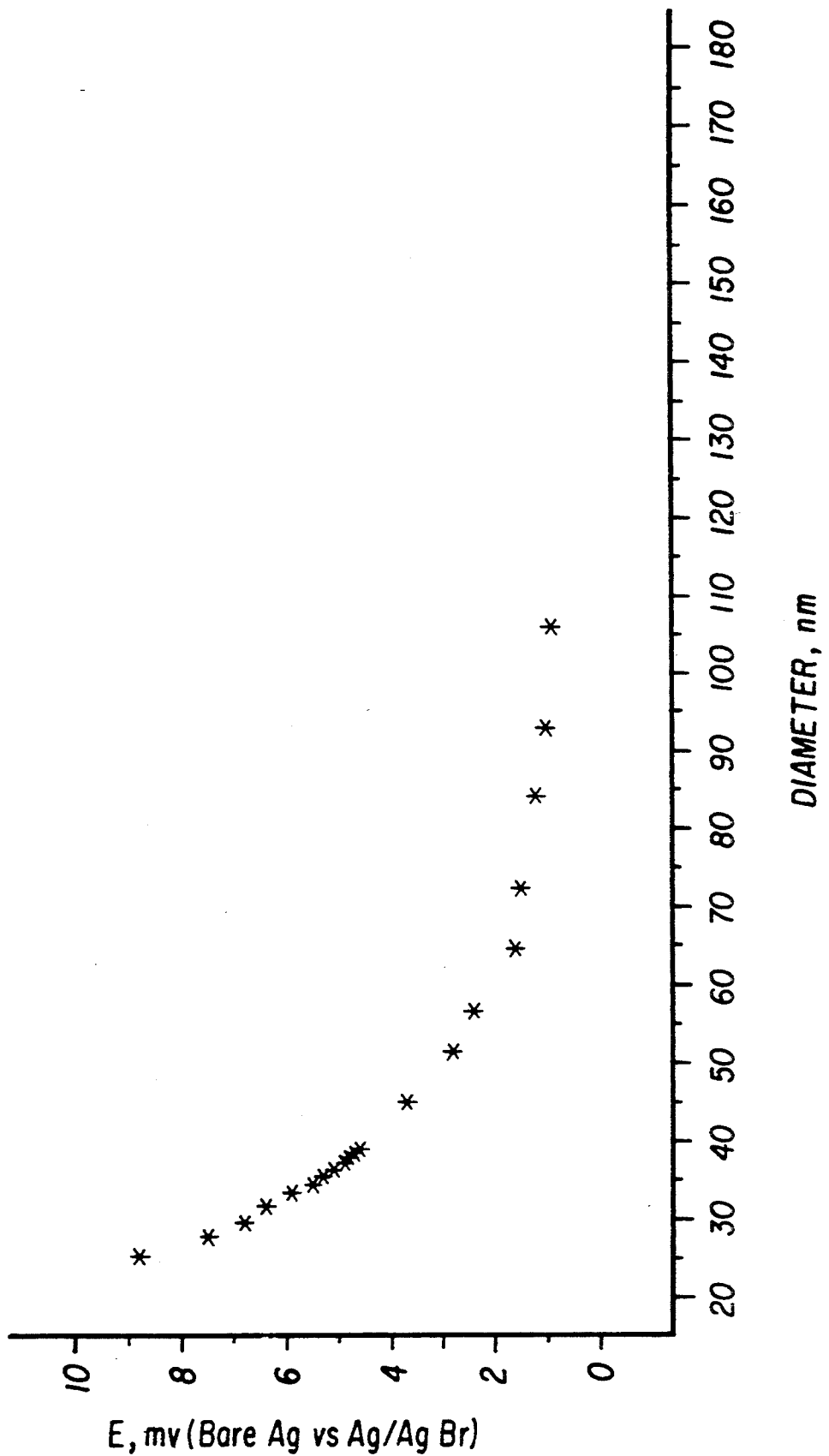

PARTICLE SIZE PROBE FOR SILVER HALIDE EMULSION

This is a Continuation of application Ser. No. 07/912,941, filed Jul. 13, 1992 now abandoned.

FIELD OF THE INVENTION

This invention relates to a process and apparatus for the determination of particle size of silver halide in a solution containing excess halide ions. More particularly, the present invention allows the determination of the average silver halide particle size within a photographic emulsion.

BACKGROUND OF THE INVENTION

An important element in the quality of silver halide emulsions is the size of the particles. It is highly desirable to have the capability of monitoring the size of the particles during the emulsion precipitation process, particularly during the early stage (nucleation) which largely dictates the end result.

In most cases the diameters of the nuclei are less than 0.1 micrometer. Methods suitable for measuring particle sizes in this size range can be found in the literature; small angle x-ray scattering, sedimentation field flow fractionation, proton correlation spectroscopy, ultracentrifugation, angular light scattering, turbidimetry, and size exclusion chromatography. Of the methods listed, turbidimetry is the most promising for on-line measuring purposes. However, it suffers interference from air bubbles which are inherent in agitated emulsion reactors. A second drawback is that the measurement from this method is in principle biased towards large particles in a population, giving high results rather than average results. This situation gets worse with wider particle size disparity.

The present invention overcomes the problems of the previous methods with a device that is easily manufactured. The apparatus of the present invention is a probe that measures the particle size of silver halide emulsions based on their relationship with solubility.

SUMMARY OF THE INVENTION

The present invention is a method and apparatus for determining the average particle size of silver halide grains in a solution containing silver ions and excess halide ions. The method includes measuring the electric potential of silver ions in solution ($E_d$) and measuring the electric potential of silver ions in solution with infinitely large silver halide particles ($E_e$). The molecular volume of the solute (v) is determined and the average particle size (d) of the silver halide grains is determined by the following equation:

$$d = \frac{4vs}{F(E_d - E_e)}$$

wherein F is the Faraday constant and (s) is the surface energy of the average particle size per unit area.

The apparatus to carry out this method comprises a metallic silver electrode for measuring potential of the silver ion in solution and a silver electrode coated with silver halide to measure the potential of the silver ion in solution with infinitely large silver halide particles. A means to calculate the molecular volume and the average particle size are also provided.

BRIEF DESCRIPTION OF THE DRAWINGS

FIG. 3 shows a plot of the measured electric potential differential of the electrode pair of the present invention versus particle size for a silver bromide emulsion.

Figure 1:
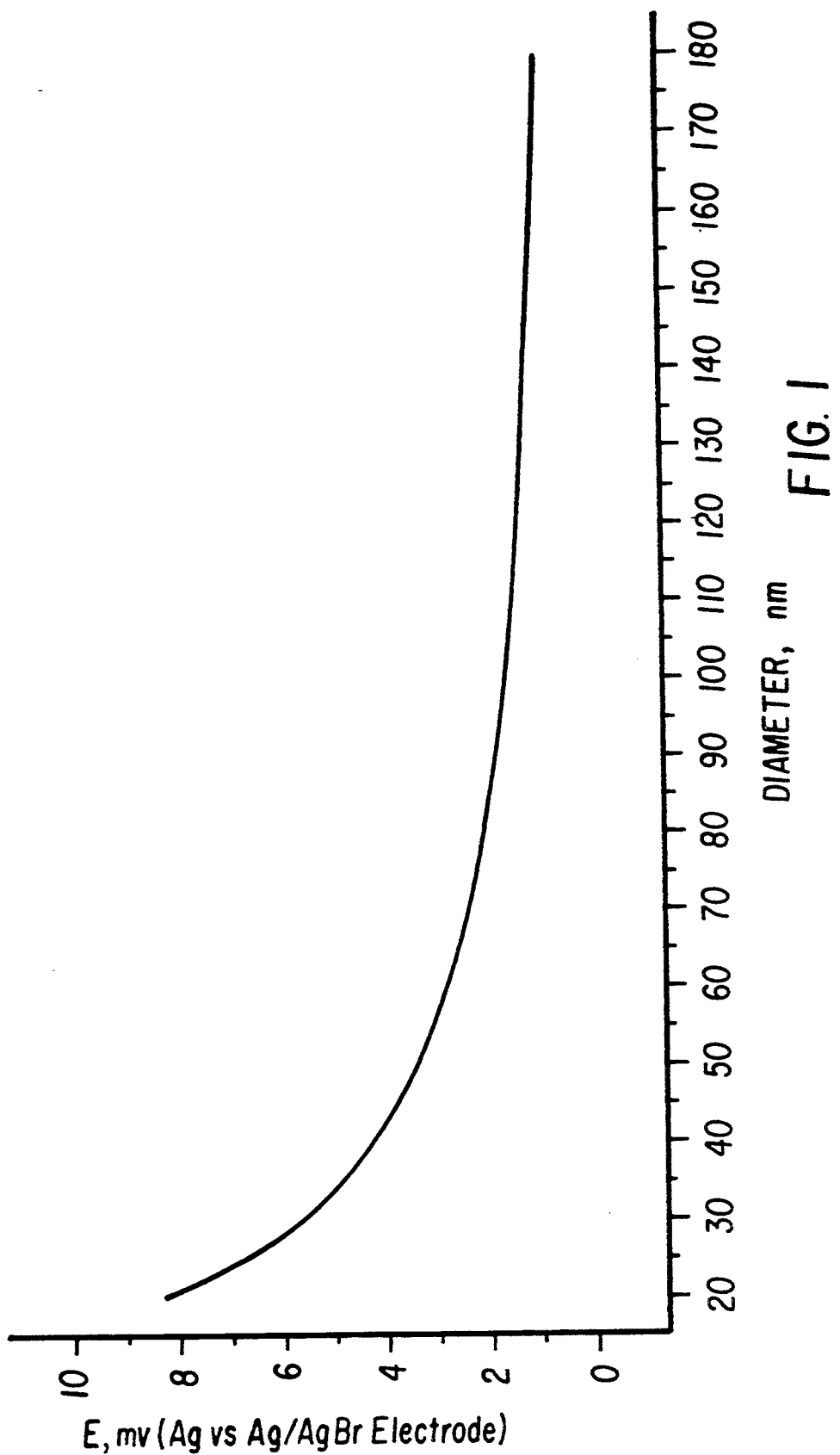
FIG. 1 shows a plot of the predicted electric potential differential for the electrode pair of the present invention versus particle size using silver bromide.

For a better understanding of the present invention together with other objects, advantages, and capabilities thereof, reference is made to the following description and appended claims in connection with the above-described drawing.

DESCRIPTION OF THE PREFERRED EMBODIMENT

The present invention describes a method and apparatus for measuring the particle size of silver halide emulsions based on their relationship with solubility. For sparingly soluble salts such as silver halide, the solubility varies with particle size as described by the Gibbs-Thomson effect. A commonly used equation is:

$$a_d = a_e \exp(4vs/RTd) \tag{1}$$

where $a_d$ = activity of the solute in equilibrium with particles of diameter d, [gm/cm$^3$]:

$a_e$ = activity of the solute when d is infinitely large [gm/cm$^3$];

v = molecular volume of the solute [cm$^3$/mole];

s = surface energy of the particle per unit area [erg/cm$^2$];

R = gas constant [erg/(mole.° K.)]; and

T = absolute temperature [° K.].

For equation (1), the activity of the solute when d is infinitely large ($a_d$) is generally referred to as the solubility. As particle size becomes infinitely large, i.e. d approaches infinity, then $a_e = a_d$. When particle size is small, then the activity of the solute $a_d$ is higher than $a_e$.

In the case of silver halide particles equilibrated with a solution containing excess halide, the activity of silver ion is measurable by a silver electrode as shown by equation (2):

$$a_d = \exp((E_d - E_o)F/RT) \tag{2}$$

where $E_d$ is the electric potential in equilibrium with particles of a diameter d;

$E_o$ is the standard potential of a Ag-Ag$^+$ couple; and

F = the Faraday constant.

When a silver electrode is coated with a layer of coarse silver halide, the electrode potential corresponds to silver ion activity at the silver-silver solution interface. A traditional way of preparing an electrode coated with silver halide is by subjecting a silver piece to the anodic potential in halide solution. The silver halide layer thus generated comprises large particles. When placed in a solution containing excess halide, this electrode produces a potential that corresponds to $a_e$, silver ion activity in equilibrium with infinitely large particles, hence:

$$a_e = \exp((E_e - E_o)F/RT) \tag{3}$$

Here $E_e$ is the potential of the silver-silver halide electrode in the presence of an excess of halide. This potential does not change with the actual silver ion activity in the solution.

Combining equations 1 through 3 gives the following expression:

$$E_d - E_e = 4vs/dF \qquad (4)$$

Equation 4 suggests that the potential difference between a silver electrode and a silver-silver halide electrode placed in the solution containing silver halide particles in equilibrium with excess halide is inversely proportional to the diameter d of the particles, and that particle size d can be inferred by measuring ($E_d - E_e$).

The above statement assumes the knowledge of v, the molecular volume and s, the surface energy. The molar volume can be determined by dividing the grams per mole of silver halide by the density of the silver halide in grams/cm$^3$.

The surface energy is not as easily determined for silver halide particles. The surface energy can range from 80–180 ergs/cm$^2$ depending on the source of the information. Therefore in the present invention, the surface energy should be determined during calibration.

FIG. 1 shows a plot of ($E_d - E_e$) versus d for silver bromide at 40° C. using 140 ergs/cm$^2$ and $4.8 \times 10^{-23}$ cm$^3$/molecule for s and v respectively. This is the predicted response for silver bromide using Equation 4.

In practice, exact surface energy is not always available. Even when it is available, the value may vary with particle size. Therefore it is advisable to use equation 4 as a general guideline and calibrate the system with a reference. In the example shown below, a turbidimeter was used to determine particle size up to 40 nm. After ripening, the final particle size was determined by an electron micrograph.

In general, this proposed approach offers the advantages of simplicity of equipment, and insensitivity to air bubbles as well as on-line capability. Also, since the electrode measures the silver ion activity that represents the average solubility of a population, an additional advantage is that the average particle size is given.

This method is applicable to all silver halide emulsions. The electrode potentials $E_d$ and $E_e$ are obtained from silver and silver halide coated electrodes respectively. Each electrode can be measured against a reference electrode separately and then the difference, $E_d - E_e$ can be calculated. An easier way, is to have the paired electrodes measured against each other to eliminate the need for a reference electrode.

It should be noted that the precision needed for the measurement of electrode potential is a fraction of one millivolt or better. This means that baseline correction resulting from the reproducibility of the electrode preparation is generally required. Typically, electrodes prepared carefully are reproducible within a few tenths of a millivolt, which means $E_d - E_e$ may not be zero when placed in an emulsion of infinitely large d. This problem can be obviated by predetermining the baseline value for the pair of electrodes using emulsions with large size particles.

The electrode for measuring the potential of the silver ion in solution can be silver, silver sulfide or a silver-noble metal alloy. The electrode for measuring the potential of the silver ion in solution in equilibrium with infinitely large silver halide particles can be a silver electrode coated with silver halide or a solid state silver halide electrode. Such an electrode is available from Corning or Orion Research.

EXAMPLE 1

Figure 2:
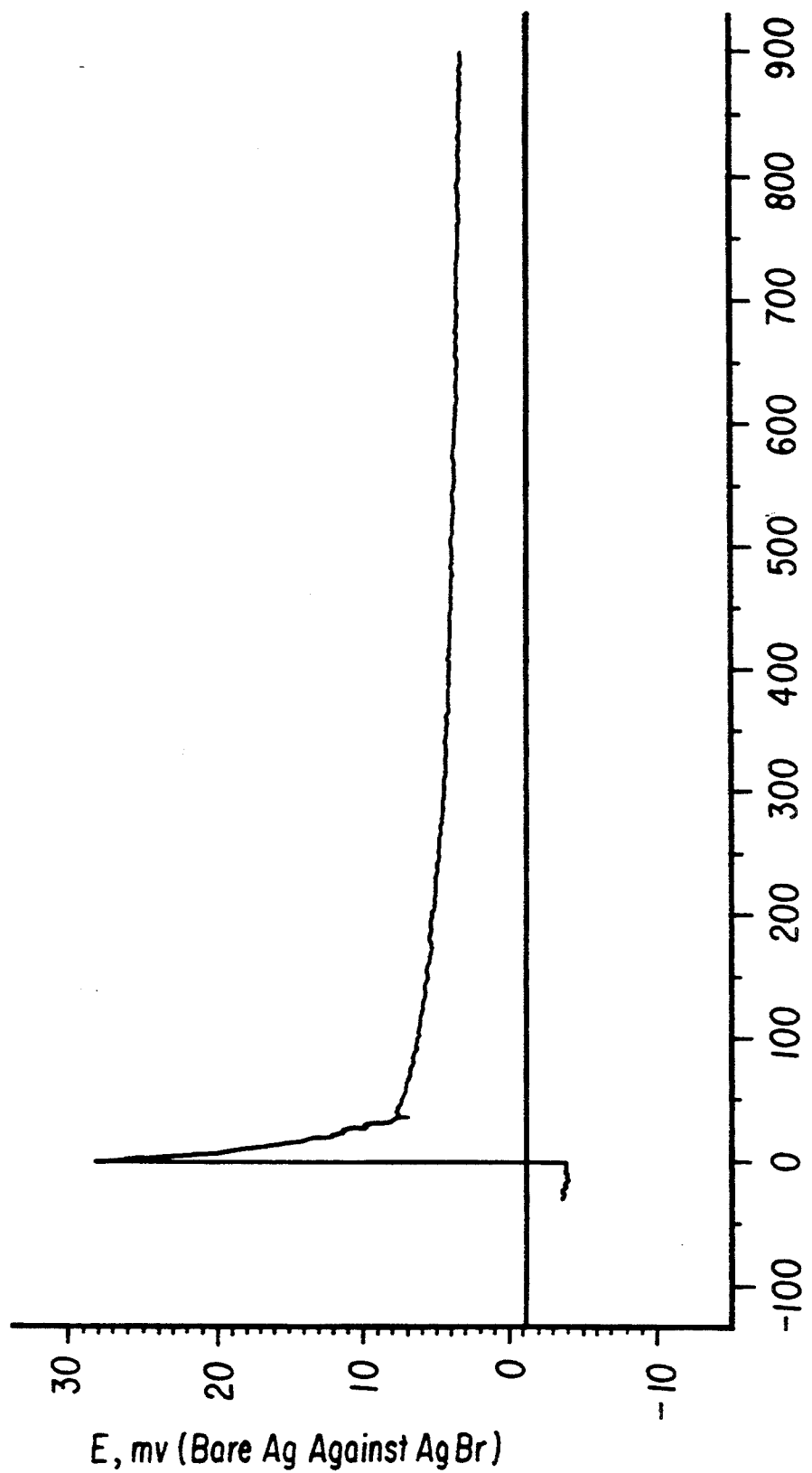
FIG. 2 shows the electric potential of the electrode pair of the present invention versus time using silver bromide.

To demonstrate the on-line capability, a batch of silver bromide nuclei of 25 nm size was made at 40° C. and the probe (Ag, Ag/AgBr) electrode pair was placed in the emulsion to monitor the size increase due to ripening. FIG. 2 shows the continuous trace recorded along with the predetermined baseline. In parallel, particle size was monitored with a turbidimeter. The ripening slows down after ten minutes when the particles grow to approximately 40 nm. Between 25 nm and 40 nm the particle size was measured by a turbidimeter. Between 40 and 100 nm actual particle size was not measured. At this point, when the particles reach a size of approximately 40 nm, the turbidimeter was turned off and the particles were allowed to grow by adding fresh silver nitrate and sodium bromide until they reached the size of 100 nm. The end size (100 nm) was verified with an electron micrograph.

The resultant plot of ($E_d - E_e$) versus d is shown in FIG. 3. FIG. 1 shows the predicted potential versus particle size for a silver bromide emulsion. As can be seen from FIGS. 1 and 3, the predicted results agree with the experimental results. If this were not the case, the value used for surface energy of the particles would be adjusted. For other silver halides, this initial calibration has to be done to get a good approximation of surface energy.

While there has been shown what are at present believed to be the preferred embodiments of the invention, it will be obvious to those skilled in the art that various alterations and modifications may be made therein without departing from the scope of the invention.

What is claimed:

1. A method for determining the average particle size of silver halide grains in solution containing silver ions and excess halide ions comprising:
   measuring the potential of the silver ion in the solution ($E_d$);
   measuring the potential of the silver ion in solution in equilibrium with theoretically infinitely large silver halide particles ($E_e$);
   determining the molecular volume (v) of the solute of the solution;
   determining the average particle size (d) of the silver halide grains in solution using the following equation $$d = \frac{4vs}{F(E_d - E_e)}$$

wherein F is the Faraday constant and (s) is the surface energy of the average particle of size per unit area; and
   outputting the average particle size (d).

2. The method according to claim 1 wherein the potential of the silver ion in solution ($E_d$) is measured by a metallic silver electrode in contact with the solution.

3. The method according to claim 1 wherein the potential of the silver ion in solution ($E_d$) is measured by a silver sulfide electrode in contact with the solution.

4. The method according to claim 1 wherein the potential of the silver ion in solution ($E_d$) is measured by a silver-noble metal electrode in contact with the solution.

5. The method according to claim 1 wherein the potential of the silver ion in solution in equilibrium with theoretically infinitely large silver halide particles ($E_e$) is measured by a silver electrode coated with silver halide which is in contact with the solution.

6. The method according to claim 1 wherein the potential of the silver ion in equilibrium with theoretically infinitely large silver halide particles ($E_e$) is measured by a silver halide solid state electrode in contact with the solution.

7. The method according to claim 1 wherein the surface energy of the average particle size per unit area is assumed to be 140 erg/cm$^2$.

8. The method according to claim 1 wherein the solution is a silver halide emulsion.

9. An apparatus for determining the average particle size of silver halide grains in a medium containing silver ions and excess halide ions comprising:
   a vessel capable of confining the medium;
   means mounted in the vessel to sense the potential of the silver ion in solute ($E_d$);
   means mounted in the vessel to sense the potential of the silver ion in solution in equilibrium with theoretically infinitely large silver halide particles ($E_e$);
   means to calculate the molecular volume (v) of the solute of the medium;
   means to calculate the average particle size of the silver halide grains in the medium using the following:

$$d = \frac{4vs}{F(E_d - E_e)}$$

wherein F is the Faraday constant and (s) is the surface energy of the average particle size per unit area; and
   means to output the average particle size (d).

10. The apparatus according to claim 9 wherein the means mounted in the vessel to sense the potential of the silver ion in solute ($E_d$) comprises:
   a metallic silver electrode in contact with the medium.

11. The apparatus according to claim 9 wherein the means mounted in the vessel to sense the potential of the silver ion in solute ($E_d$) comprises:
   a silver sulfide electrode in contact with the medium.

12. The apparatus according to claim 9 wherein the means mounted in the vessel to sense the potential of the silver ion in solute ($E_d$) comprises:
   a silver-noble metal alloy electrode in contact with the medium.

13. The apparatus according to claim 9 wherein the means mounted in the vessel to sense the potential of the silver ion in solution in equilibrium with theoretically infinitely large particles of silver halide comprises:
   a metallic silver electrode coated with silver halide in contact with the medium.

14. The apparatus according to claim 9 wherein the means mounted in the vessel to sense the potential of the silver ion in solution in equilibrium with theoretically infinitely large particles of silver halide comprises:
   a solid state silver halide electrode in contact with the medium.

15. The apparatus according to claim 9 wherein the surface energy per unit area of an average particle is 140 erg/cm$^2$.

16. The apparatus according to claim 9 wherein the surface energy per unit area of an average particle is determined experimentally.

17. The apparatus according to claim 9 wherein the medium is a silver halide emulsion.

18. A method for ripening silver halide grains in solution containing silver ions and excess halide ions comprising:
   providing silver halide nuclei in the solution;
   adding silver nitrate to the solution;
   adding halide salt to the solution;
   measuring the potential of the silver ions in the solution ($E_d$);
   measuring the potential of the silver ions in solution in equilibrium with theoretically infinitely large silver halide particles ($E_e$);
   determining the molecular volume (v) of the solute of the solution; and
   determining the average particle size (d) of the silver halide grains in solution using the following equation $$d = \frac{4vs}{F(E_d - E_e)}$$

wherein F is the Faraday constant and (s) is the surface energy of the average particle size per unit area; and
   stopping the addition of silver nitrate and halide salt when the average particle size (d) has reached a predetermined value.

19. The method according to claim 18 wherein the surface energy of the average particle size per unit area is approximately 140 erg/cm$^2$.

20. The method according to claim 18 wherein the solution is a silver halide emulsion.

* * * * *